United States Patent [19]

Bracht et al.

[11] Patent Number: 5,780,449
[45] Date of Patent: Jul. 14, 1998

[54] CATHEPSIN G-INHIBITING APTAMERS

[75] Inventors: Franzpeter Bracht, Düsseldorf; Karsten Schrör, Frechen-Königsdorf, both of Germany

[73] Assignee: Crinos Industria Farmacobiologica S.P.A., Villa Guardia, Italy

[21] Appl. No.: 753,054

[22] Filed: Nov. 19, 1996

[30] Foreign Application Priority Data

Nov. 24, 1995 [DE] Germany ............ 195 43 750.0

[51] Int. Cl.⁶ .................. A61K 31/70; C07H 21/04
[52] U.S. Cl. .................. 514/44; 536/24.5; 435/6
[58] Field of Search .................. 536/24.5; 514/44; 435/6

[56] References Cited

U.S. PATENT DOCUMENTS

| | | | |
|---|---|---|---|
| 5,217,951 | 6/1993 | Lezdey et al. | 514/8 |
| 5,290,762 | 3/1994 | Lezdey et al. | 514/8 |
| 5,510,333 | 4/1996 | Angelastro et al. | 514/18 |
| 5,514,694 | 5/1996 | Powers et al. | 514/357 |
| 5,612,194 | 3/1997 | Rubin et al. | 435/69.2 |

OTHER PUBLICATIONS

Krieg et al., "CpG Motifs in Bacterial DNA Trigger Direct B-Cell Activation," *Nature*, 374, 546–549 (6 Apr. 1995).

*Primary Examiner*—John Kight
*Assistant Examiner*—L. Eric Crane
*Attorney, Agent, or Firm*—Sprung Kramer Schaefer & Briscoe

[57] ABSTRACT

Cathepsin G-inhibiting aptamers comprising oligonucleotides selected from the group consisting of the consensus sequences:

$GGN_{1-7}GGN_{8-14}GGN_{1-6}GGN_{1-7}GGN_{1-6}GG$ (SEQ ID NO: 1)
$GGN_{10-13}GGN_{1-5}GGN_{1-5}GGN_{3-6}GGN_{2-7}GG$ (SEQ ID NO: 2)
and the sequence

GGGTTGAGGGTGGATTACGCCACGT (SEQ ID NO: 3)

GGAGCTCGGATCCACACATCCAGG wherein N represents nucleotides and the figures represent the number of possible nucleotides at that site; said cathepsin G-inhibiting aptamers are suggested as medicament.

3 Claims, 4 Drawing Sheets

CATHEPSIN G-INHIBITING APTAMERS

DESCRIPTION

The invention concerns cathepsin G-inhibiting oligonucleotides and medicaments containing them.

Cathepsin G is a serine protease which is similar to chymotrypsin and which is primarily located in the azurophilic granules of polymorphonuclear leucocytes (PMN). That enzyme is liberated during PMN-degranulation, it stimulates platelet aggregation and it hydrolyses proteoglycanes, glycoproteins and collagen in the vessel wall. Further cells circulating in the blood, in particular leucocytes, are activated. A further aspect of significance is that cathepsin G is involved in the activation of coagulation factors such as factor V and in the proteolytic activation of the human platelet-glycoproteins Ib-IX and IIb/IIIa. The platelet-stimulating action of cathepsin G is similar to that of thrombin but differs therefrom by virtue of the fact that it is afforded by way of separate mechanisms (receptors). In addition cathepsin G release can result in damage to the cell wall and other tissue.

In addition a large number of further effects on the part of cathepsin G is known, so that in summary it can be noted that cathepsin G is liberated during the degranulation of PMN, it splits biologically important proteins and thus contributes to tissue damage during inflammatory and ischaemic occurrences. The previous findings regarding the effects of cathepsin G lead to the assumption that the inhibition of cathepsin G is suitable for the treatment and prophylaxis of inflammatory occurrences and procoagulant conditions.

Known cathepsin G antagonists are the proteins eglin B and C (Handbook of Enzyme Inhibitors, 2nd edition, published by Chemie Weinheim, 1993) which however cannot be used orally as medicaments and which involve the significant risk of immunological complications. Further inhibitors such as heparin are not selective and also inhibit other enzymes such as thrombin.

The object of the present invention is therefore that of providing cathepsin G inhibitors and medicaments containing them.

That object is attained by cathepsin G-inhibiting aptamers comprising oligonucleotides selected from the group consisting of the consensus sequences:

$GGN_{1-7}GGN_{8-14}GGN_{1-6}GGN_{1-7}GGN_{1-6}GG$ (SEQ ID NO: 1)
$GGN_{10-13}GGN_{1-5}GGN_{1-5}GGN_{3-6}GGN_{2-7}GG$ (SEQ ID NO: 2)
and the sequence

GGGTTGAGGGTGGATTACGCCACGT (SEQ ID NO: 3)

GGAGCTCGGATCCACACATCCAGG wherein N represents further nucleotides and the figures represent the number of possible nucleotides at that site.

The consensus sequences were ascertained by considering the G-pairs as the fixed element of the oligonucleotides. The G-pairs were detected as common structure element of the oligonucleotides having the selected primer sequences at their 5'- and 3'- termini after preparing the oligonucleotide pool which is mentioned in the preparation example. This was found out by simple comparison of the primary structure of the oligonucleotides. The G-pairs are responsible for the optimum energy structure of the tertiary structure, which in energy terms is markedly more advantageous than adequate Watson-Crick base pairings. Based on those fixed points, it was possible to ascertain the number of bases between those 'supporting elements'. In this context it is referred to Nature, Vol. 355 (1992), pgs. 564–566. It was found in this respect that except for a few exceptions the aptamers can be divided into two groups which are represented by the consensus sequences involved. The exceptions from the consensus sequences found differ from the aptamers represented by the consensus sequences by the extreme prolongation of one of the designated loops. As it is apparent from Table 1 this has no effects on the function of the oligonucleotides as cathepsin G-inhibitors. For that reason those sequences were not taken into consideration in ascertaining the consensus sequence. The consensus sequences therefore represent the sequences which give the greatest effect, with minimum length. The consensus sequences were ascertained as the optimum sequence having regard to the sequence length and the action as an inhibitor.

Those sequences are also effective as a constituent of a longer oligonucleotide with for example 90 nucleotides.

The aptamers according to the invention exhibit strong inhibition in respect of pure cathepsin G. The cathepsin G-induced stimulation of the aggregation of washed human platelets is inhibited in dependence on concentration by the cathepsin G aptamer. The aptamers according to the invention also inhibit the fMLP-stimulated liberation of $O_2$-radicals from PMN.

As denaturing of the oligonucleotides or aptamers according to the invention in the gastrointestinal tract is not to be expected, they are proposed as orally administrable medicaments.

The aptamers according to the invention are further suggested as medicaments in particular for the treatment of illnesses where neutrophilic granulocytes are activated. Such illnesses or pathological conditions include inflammatory and procoagulatory conditions. Specific indications are asthma, bronchitis, bone and cartilage illnesses and rheumatoid conditions. Other indications are the prophylaxis and treatment of intravascular coagulopathies, in particular in relation to septic shock and related illnesses, thrombotic diseases and arterial and venous vasopathies which include the PMN-induced activation of platelets, the plasmatic coagulation system and vessel damage.

Such illnesses are in particular myocardial infarctions, peripheral vessel occlusions and inflammatory and thrombotic diseases of the venous system, and reperfusion damage due to cathepsin G-dependent tissue destruction of the ischaemic heart muscle. Finally the aptamers according to the invention are proposed for prophylaxis and inhibition of the progression of Alzheimer's disease.

Preferred embodiments of the aptamers according to the invention are set out hereinafter, they all have the action which is desired. Aptamers 1 to 11 are governed by the above-specified first consensus sequence and aptamers 12 to 15 by the above specified second consensus sequence.

5'-                                                                                                                                                      3'-

1) GGTACCCGGA TCCGAGCTCC ACGTGGGGGC ACGGACTGG (SEQ ID NO: 4)
2) GGTCCTGGTG CTCCTCGTGG AGTTCGGATC CGGGG (SEQ ID NO: 5)
3) GGTCGAGGCT AGCTAGCGAG CGGTAGTCTA GAACCTTAGG (SEQ ID NO: 6)
   CGTGGTGAGG

-continued

4) GGACCTTAAG GGCACAACTG AGGAAATGGA GGTAGG (SEQ ID NO: 7)
5) GGCGCGAGGT GCACCGTTAC CAGGGTGGAT GGTACCTAGG (SEQ ID NO: 8)
6) GGRGGGTTAG TTACAAACGT AGGSACGTGG RGCTCGGATY YCSGG (SEQ ID NO: 9)
7) GGTSCTGGTS CCCYACGGTC GACSCTAGCG TAGGAAACSC CGGCTAGG (SEQ ID NO: 10)
8) GGTGGACCST ACSAGGKTTA CYKGGAWYCS AGGYCCAMST GG (SEQ ID NO: 11)
9) GGCTGGRTYC CSAGSTYCAC CGKGGGRGGR CAAMAATGGG GG (SEQ ID NO: 12)
10) GGTCGAGGTA GCTGCGAGCT CGGTGGCGTG GTGAGG (SEQ ID NO: 13)
11) GGTGAGACGG GCATGTTGTT GGBATTCGGT TGATGCTC (SEQ ID NO: 14)
    CACGTGGAGC TCGG
12) GGTGTGTACA CACATTGGCG GTGGATGAGG TCGG (SEQ ID NO: 15)
13) GGGGCGCAGT TAGGTGTGAG GTGTGAGGTC ACGTGGGCTC GG (SEQ ID NO: 16)
14) GGATGATATC CTCATGGCAG GGAATGGTGC GGGCTCCAGG (SEQ ID NO: 17)
15) GGATTTGATA TGGCAGGGAA TGGTGCGGGC TTCCCAGG (SEQ ID NO: 18)

The oligonucleotides according to the invention may occur in the form of DNA- or RNA-oligonucleotides. The sequences can be modified to increase their half-life time. In accordance with the invention, suitable for that purpose are nucleotides which are modified for example by 2'-fluorouracil or 2'-fluorocytosin, or nucleotides such as 2'-amino-CTP and 2'-amino-UTP. The oligonucleotides can also be stabilised with phosphorus thioate.

Forms of medicine which are suitable according to the invention, for administration of the aptamers, are injectable, orally administrable and topically effective preparations. Orally administrable and topically effective medicaments include in particular tablets, pills, capsules and syrups in the form of solutions or suspensions of the aptamers according to the invention as well as spreadable preparations. The production of such medicaments and the adjuvants to be used are known to the man skilled in the art.

Figure 1:
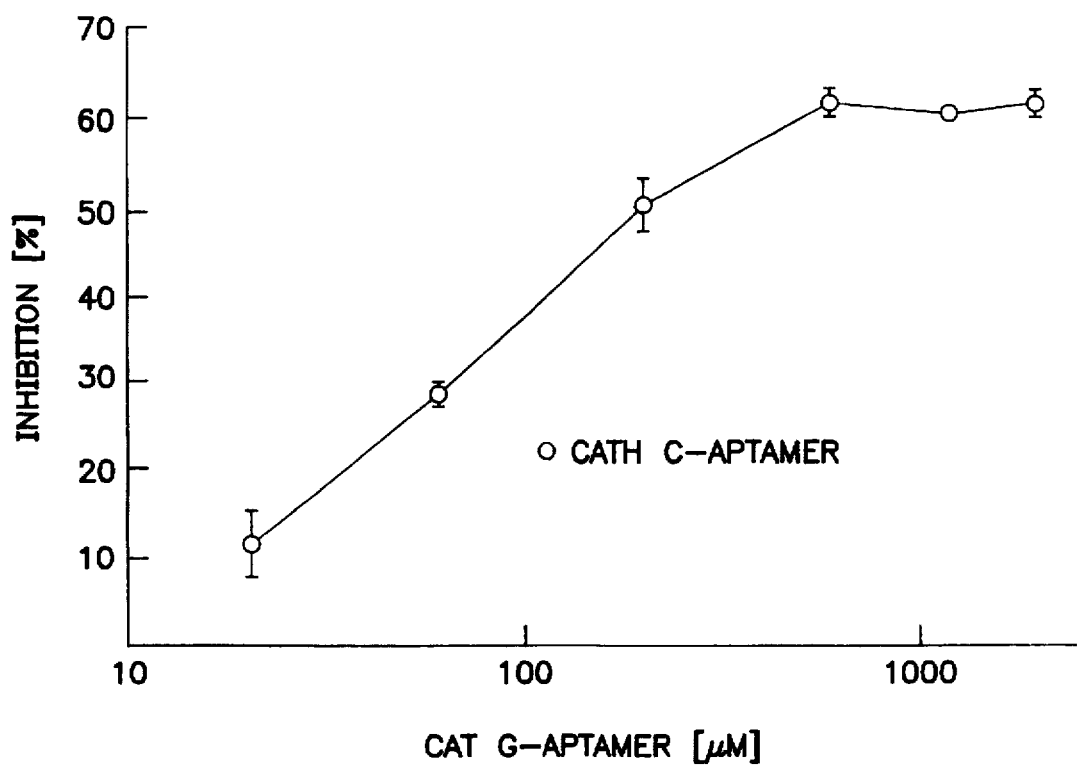
FIG. 1 shows inhibition of cathepsin G activity by aptamer 10 in a chromogenic assay with the substrate S 2545 from the company Chromogenix (Essen, Germany) (Blood, 77, (1991), 2379–2388). The cathepsin G activity was measured by reference to the hydrolysis of Suc-Ala-Ala-Prp-Phe-Pna. The activity of cathepsin G is inhibited in dependence on concentration; maximum inhibition is achieved with 60% at 300 nM aptamer concentration.
Figure 2:
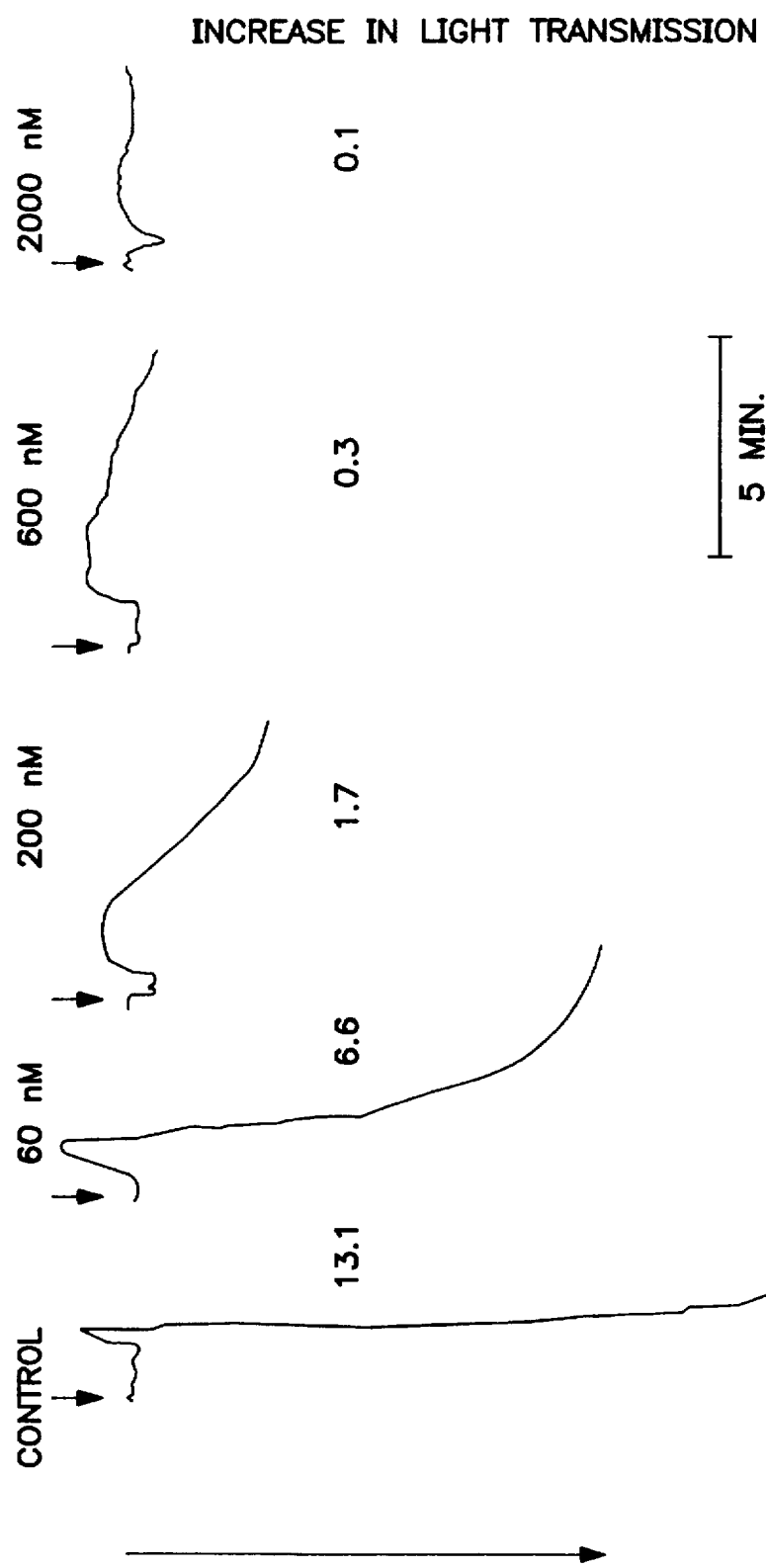
FIG. 2 illustrates the cathepsin G-induced thrombocyte aggregation inhibited by aptamer 10 (Blood, 81, (1993) 2947–2957). Once again there is a concentration-dependent inhibition on the cathepsin G-induced effect. A 90% inhibition level is achieved with an aptamer concentration of 200 nM.
Figure 3:
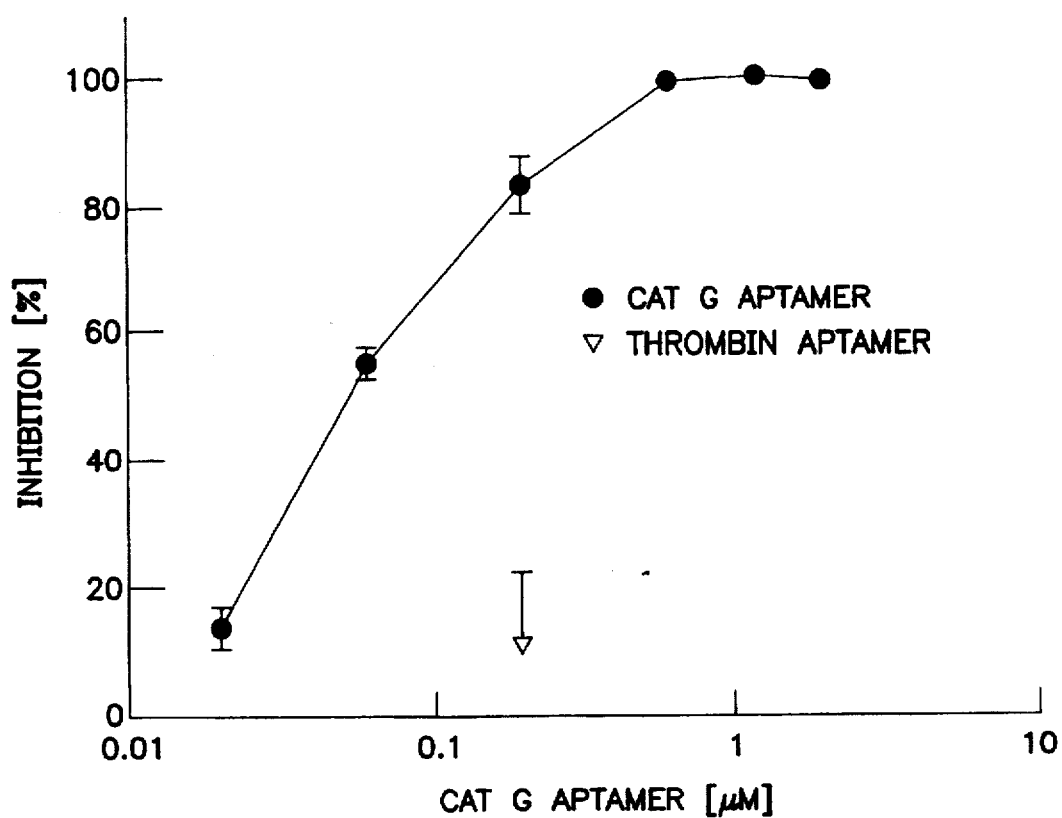
FIG. 3 shows the concentration dependency of the cathepsin G-induced thrombocyte aggregation which is inhibited by the aptamers: the findings shown in Fig.2 are substantiated here. In addition it is possible to show the absence of an inhibition effect by the thrombin-inhibiting aptamer.
Figure 4:
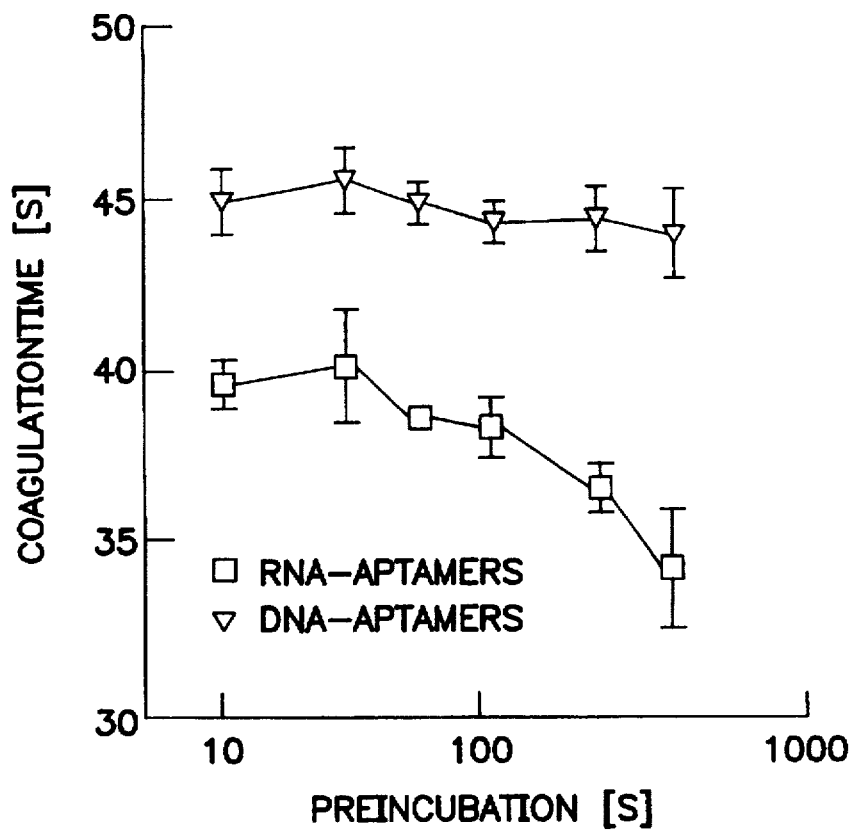
FIG. 4 shows stability of an aptamer in human plasma. There is no significant loss in activity of the aptamers during preincubation in human plasma for up to 15 minutes. This illustration demonstrates the stability of the aptamers while subjected to nucleases in plasma.

All data set out in FIGS. 1 to 4 are mean values of n=3±SD.

These biological tests show that maximum inhibition is already achieved with about 200 nM cathepsin G-aptamer. The inhibition constant $IC_{50}$ is about 60 to 100 nM, which leads to an expectation of a Ki in the lower nanomolar range.

Further, aptamers 1, 3, 5, 6, 7, 9, 10, 11, 14, and 15 were tested in order to determine their inhibitory degree. Once more basis for the tests was the inhibitory action of these aptamers on the activity of cathepsin G to split C-terminal of a substrate to aromatic aminoacids. The substrate was Succinyl-L-alanyl-L-prolyl-L-phenylalanine-p-nitroanilide (Suc-Ala-Pro-Phe-Pna). Cathepsin G was used in form assumed to be pure. Determination of activity of cathepsin G in the presence of the aptamers according to the invention was carried out in 0.03 mol/l Tris, pH 7.2, 150 mmol/l NaCl, 5 mmol $MgCl_2$ and 5 mmol KCl. The change in absorption was measured at 405 nm (2 values) and the activity of cathepsin G was calculated. In the table degree of inhibition is shown as on-inhibited control sample.

TABLE

| Aptamer: | % inhibition | |
|---|---|---|
| | experiment 1 | experiment 2 |
| 1 | 46 | 45 |
| 3 | 47 | 49 |
| 5 | 43 | 41 |
| 6 | 44 | 42 |
| 7 | 46 | 49 |
| 9 | 48 | 48 |
| 10 | 49 | 50 |
| 11 | 41 | 37 |
| 14 | 41 | 40 |
| 15 | 36 | 32 |

PREPARATION EXAMPLE

1. In vitro-selection for Isolation of Cathepsin G Binding Aptamers

The cathepsin G-inhibiting aptamer sequences according to the invention can preferably be obtained by a method which is fundamentally described in NATURE 355, 564–566 (1992) and in particular in Gene, 137 (1993), 25–31, for the isolation of single-strand DNA-nucleotides which bond and inhibit human thrombin.

1.1 Preparation of a Oligonucleotide Pool

For isolation of a previous unknown enzyme binding sequence (aptamer) a sufficient amount of synthetic oligonucleotides differing from each other is required. This oligonucleotide pool should meet the following requirements a) at least $10^{13}$ different sequences, b) the oligonucleotides must be amplifiable by way of a polymerase chain reaction (PCR), and c) possibility of directed cloning.

The required amount of different oligonucleotides is achieved, when in a molecule which has 60 nucleotides each position may be taken by each of the 4 bases A, C, G, T.

The capability of being amplified by way of PCR is obtained by linking a 18 bases of a defined sequence both at the 5'- and at the 3'-end of the 60 bases nucleotide. The possibility was directed cloning if achieved by inserting a suitable restriction intersection in the 5'-primer sequence of the oligonucleotide for the restriction nuclease Eco RI. The resulting oligonucleotide with 96 bases fulfills all indicated requirements and the sequence is shown below.

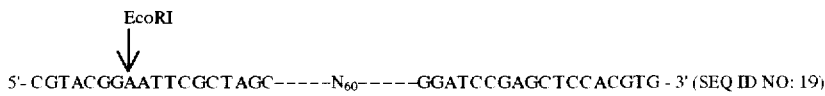

5'- CGTACGGAATTCGCTAGC-----N$_{60}$-----GGATCCGAGCTCCACGTG - 3' (SEQ ID NO: 19)

wherein N represents nucleotides. There are 60 nucleotides between those 18 bases-long primer-bonding reagents. In that reagent each of the possible bases can be on any position. That provides the number of about $10^{13}$ different sequences. This oligonucleotide is purified by way of HPLC.

1.2 Incubation of Oligonucleotides with Cathepsin G

In this preparation step DNA oligonucleotides are bound to the target enzyme and oligonucleotides which are not bound are separated by way of ion exchange chromatography.

In the first step a sufficient amount of the oligonucleotide pool (300 μg≈10 nmol) is incubated with 100 μg cathepsin G. The incubation buffer contained 30 mM Tris-HCl, 150 mM NaCl, 5 mM KCl and 5 nM $MgCl_2$, pH 7.5. Incubation was performed for 30 minutes at room temperature and the incubate has a total volume of 1 ml.

1.3 Ion Exchange Chromatography

Subsequently the incubate was subjected to a 1 ml Hightrap SP-cation exchanger column, Pharmacia. The column material had been previously balanced with the incubation buffer. Further equipment which was used in this step are a membrane pump and a spectral photometer and a recording device.

After further incubating for about 25 minutes at 4° C. DNA-fragments which were not bound were washed out (flow rate 1 ml/min.) whereas the positively charged cathepsin G with bound to DNA-fragments rested on the column material. Eluation of the DNA/enzyme complex bound to the column material was effected with 0.8M NaCl and 50 mM tris-HCl-buffer, pH 7.8 (flow rate 0.5 ml/min.). Fractions which were photometrically identified as containing DNA were collected and subjected to known ethanol/acetate-precipitation in accordance with Sambrook, Fritsch and Maniatis, Molecular Cloning, Cold Spring Harbor, Laboratory Press, (1989). Three times the volume of ethanol was added. After precipitation over night at −20° C., centrifuging was effected at 12000×g for 1 hour (Heraeus Biofuge 13). The pellet obtained was dried and diluted in 50 μl sterile $H_2O$. The following polymerase chain reaction was performed with 15μl DNA solution, accordingly up to 3 amplifications could be performed with one fraction.

1.4 Polymerase Chain Reaction

Polymerase chain reaction was performed with the primers 5'-CGTACGGAATTCGCTAGC-3' (SEQ ID NO: 20) and 5'-CACGTGGAGCTCGGATCC-3'(SEQ ID NO 21). The conditions for maximal amplification of eluted DNA were previously determined in test series. Optimum $MgCl_2$ concentration was 2 mM, optimum primer concentration was 1.5 μM. Besides that, a PRIMEZYME-kit of Biometra including polymerase and buffers as well as $MgCl_2$ solution was used. The temperature for denaturation was 94° C., the temperature for hybridization of the primer about 42° C. and for elongation 72° C. (1 minute), respectively. The use of 1 U polymerase was sufficient in order to allow maximal yield. 40 of such cycles were performed. The product of these reactions was analysed by way of agarose gel electrophoresis and quantified by comparison with the DNA elongation standard. Subsequently it was precipitated, taken up in distilled water and then by way of thermal denaturation (95° C.) transformed to the single stranded form. This is the end of a cycle; then DNA was once more transferred to the above described incubation.

1.5 Avoiding of Enrichment of DNA-sequences Bound Unspecifically to the Column Material In order to prevent an enrichment of sequences bonding to the column material the process was modified in the last 3 cycles. DNA was not preincubated with cathepsin G but the enzyme directly loaded on the chromatographic column. A further column preswitched was only filled with cation exchanger material and assured that by subsequent loading of DNA (flow rate 0.3 ml/min) only those fragments could bind to cathepsin, which did not unspecifically react with the column material of the first column.

1.6 Cloning and Sequencing of the PCR Product after the Last Cycle

After the last cycle the resulting PCR product was completed with a Klenow-polymerase, phosphorylation was effected and the mixture subjected to EcoR1 restriction. Then directed cloning into the vector pUC18 was performed. After, sequencing homologes were searched within the sequenced inserts. The sequences obtained were evaluated by means of a computer program (Husar, EMBL Database, Heidelberg).

We claim:

1. An oligonucleotide consisting of a nucleotide sequence selected from the group consisting of:

a) the sequence:

GGGTTGAGGGTGGATTACGCCACGT

GGAGCTCGGATCCACACATCCAGG, which has been designated SEQ ID NO.: 3; and b) the consensus sequences:

$GGN_{1-7}GGN_{8-14}GGN_{1-6}GGN_{1-7}GGN_{1-6}GG$; and
$GGN_{10-13}GGN_{1-5}GGN_{1-5}GGN_{3-6}GGN_{2-7}GG$, which have been designated SEQ ID NO.: 1 and SEQ ID NO.: 2, respectively;

wherein the Ns are identical or different and each represents a nucleotide independently selected from the group consisting of dA, dC, dT and dG;

and wherein the subscript figures indicate the number of times that N appears consecutively at the indicated positions within the nucleotide sequence.

2. A pharmaceutical composition comprising an amount of an oligonucleotide according to claim 1, said amount being effective to inhibit cathepsin-G, and a pharmaceutically acceptable carrier.

3. A method of inhibiting cathepsin G in a patient in need thereof, comprising administering to said patient an amount of an oligonucleotide according to claim 1, said amount being effective to inhibit cathepsin-G.

* * * * *

SEQUENCE LISTING ( 1 ) GENERAL INFORMATION:

( i i i ) NUMBER OF SEQUENCES: 21

( 2 ) INFORMATION FOR SEQ ID NO: 1:

( i ) SEQUENCE CHARACTERISTICS:
      ( A ) LENGTH: 52 Nucleotides
      ( B ) TYPE: Nucleotide
      ( C ) STRANDEDNESS: Single
      ( D ) TOPOLOGY: Linear ( i x ) FEATURE:
      ( D ) OTHER INFORMATION:Nucleotides 3- 9, 11-25 and 36-43 could
      be six nucleotides shorter; 28-33 and
      45-50 five nucleotides shorter ( x i ) SEQUENCE DESCRIPTION: SEQ ID NO: 1:

GGNNNNNNNG GNNNNNNNNN NNNNGGNNN NNNGGNNNNN  40

NNGGNNNNNN GG  52

( 2 ) INFORMATION FOR SEQ ID NO: 2:

( i ) SEQUENCE CHARACTERISTICS:
        ( A ) LENGTH: 48 Nucleotides
        ( B ) TYPE: Nucleotide
        ( C ) STRANDEDNESS: Single
        ( D ) TOPOLOGY: Linear ( i x ) FEATURE:
        ( D ) OTHER INFORMATION:Nucleotides 3- 15 and 32-37 could be
            three nucleotides shorter; 18-22 and
            25-29 four nucleotides shorter; 40-46
            five nucleotides shorter ( x i ) SEQUENCE DESCRIPTION: SEQ ID NO: 2:

GGNNNNNNNN NNNNGGNNN NNGGNNNNNG GNNNNNNGGN  40

NNNNNNGG  48

( 2 ) INFORMATION FOR SEQ ID NO: 3:

( i ) SEQUENCE CHARACTERISTICS:
        ( A ) LENGTH: 49 Nucleotides
        ( B ) TYPE: Nucleotide
        ( C ) STRANDEDNESS: Single
        ( D ) TOPOLOGY: Linear ( x i ) SEQUENCE DESCRIPTION: SEQ ID NO: 3:

GGGTTGAGGG TGGATTACGC CACGTGGAGC TCGGATCCAC  40

ACATCCAGG ( 2 ) INFORMATION FOR SEQ ID NO: 4:

( i ) SEQUENCE CHARACTERISTICS:
        ( A ) LENGTH: 39 Nucleotides
        ( B ) TYPE: Nucleotide
        ( C ) STRANDEDNESS: Single
        ( D ) TOPOLOGY: Linear ( x i ) SEQUENCE DESCRIPTION: SEQ ID NO: 4:

GGTACCCGGA TCCGAGCTCC ACGTGGGGGC ACGGACTGG  39

( 2 ) INFORMATION FOR SEQ ID NO: 5:

( i ) SEQUENCE CHARACTERISTICS:
        ( A ) LENGTH: 35 Nucleotides
        ( B ) TYPE: Nucleotide
        ( C ) STRANDEDNESS: Single
        ( D ) TOPOLOGY: Linear ( x i ) SEQUENCE DESCRIPTION: SEQ ID NO: 5:

GGTCCTGGTG CTCCTCGTGG AGTTCGGATC CGGGG  35

( 2 ) INFORMATION FOR SEQ ID NO: 6:

( i ) SEQUENCE CHARACTERISTICS:
        ( A ) LENGTH: 50 Nucleotides
        ( B ) TYPE: Nucleotide
        ( C ) STRANDEDNESS: Single
        ( D ) TOPOLOGY: Linear ( x i ) SEQUENCE DESCRIPTION: SEQ ID NO: 6:

```
GGTCGAGGCT AGCTAGCGAG CGGTAGTCTA GAACCTTAGG                    40

CGTGGTGAGG                                                    50
```

( 2 ) INFORMATION FOR SEQ ID NO: 7:

( i ) SEQUENCE CHARACTERISTICS:
        ( A ) LENGTH: 36 Nucleotides
        ( B ) TYPE: Nucleotide
        ( C ) STRANDEDNESS: Single
        ( D ) TOPOLOGY: Linear ( x i ) SEQUENCE DESCRIPTION: SEQ ID NO: 7:

```
GGACCTTAAG GGCACAACTG AGGAAATGGA GGTAGG                       36
```

( 2 ) INFORMATION FOR SEQ ID NO: 8:

( i ) SEQUENCE CHARACTERISTICS:
        ( A ) LENGTH: 40 Nucleotides
        ( B ) TYPE: Nucleotide
        ( C ) STRANDEDNESS: Single
        ( D ) TOPOLOGY: Linear ( x i ) SEQUENCE DESCRIPTION: SEQ ID NO: 8:

```
GGCGCGAGGT GCACCGTTAC CAGGGTGGAT GGTACCTAGG                   40
```

( 2 ) INFORMATION FOR SEQ ID NO: 9:

( i ) SEQUENCE CHARACTERISTICS:
        ( A ) LENGTH: 45 Nucleotides
        ( B ) TYPE: Nucleotide
        ( C ) STRANDEDNESS: Single
        ( D ) TOPOLOGY: Linear ( x i ) SEQUENCE DESCRIPTION: SEQ ID NO: 9:

```
GGRGGGTTAG TTACAAACGT AGGSACGTGG RGCTCGGATY                   40

YCSGG                                                         45
```

( 2 ) INFORMATION FOR SEQ ID NO: 10:

( i ) SEQUENCE CHARACTERISTICS:
        ( A ) LENGTH: 48 Nucleotides
        ( B ) TYPE: Nucleotide
        ( C ) STRANDEDNESS: Single
        ( D ) TOPOLOGY: Linear ( x i ) SEQUENCE DESCRIPTION: SEQ ID NO: 10:

```
GGTSCTGGTS CCCYACGGTC GACSCTAGCG TAGGAAACSC                   40

CGGCTAGG                                                      48
```

( 2 ) INFORMATION FOR SEQ ID NO: 11:

( i ) SEQUENCE CHARACTERISTICS:
        ( A ) LENGTH: 42 Nucleotides
        ( B ) TYPE: Nucleotide
        ( C ) STRANDEDNESS: Single
        ( D ) TOPOLOGY: Linear ( x i ) SEQUENCE DESCRIPTION: SEQ ID NO: 11:

```
GGTGGACCST ACSAGGKTTA CYKGGAWYCS AGGYCCAMST                   40

GG                                                            42
```

( 2 ) INFORMATION FOR SEQ ID NO: 12:

( i ) SEQUENCE CHARACTERISTICS:
        ( A ) LENGTH: 42 Nucleotides ( B ) TYPE: Nucleotide
( C ) STRANDEDNESS: Single
( D ) TOPOLOGY: Linear ( x i ) SEQUENCE DESCRIPTION: SEQ ID NO: 12:

GGCTGGRTYC CSAGSTYCAC CGKGGGRGGR CAAMAATGGG    40

GG    42

( 2 ) INFORMATION FOR SEQ ID NO: 13:

( i ) SEQUENCE CHARACTERISTICS:
( A ) LENGTH: 36 Nucleotides
( B ) TYPE: Nucleotide
( C ) STRANDEDNESS: Single
( D ) TOPOLOGY: Linear ( x i ) SEQUENCE DESCRIPTION: SEQ ID NO: 13:

GGTCGAGGTA GCTGCGAGCT GGGTGGCGTG GTGAGG    36

( 2 ) INFORMATION FOR SEQ ID NO: 14:

( i ) SEQUENCE CHARACTERISTICS:
( A ) LENGTH: 52 Nucleotides
( B ) TYPE: Nucleotide
( C ) STRANDEDNESS: Single
( D ) TOPOLOGY: Linear ( x i ) SEQUENCE DESCRIPTION: SEQ ID NO: 14:

GGTGAGACGG GCATGTTGTT GGBATTCGGT TGATGCTCCA    40

CGTGGAGCTC GG    52

( 2 ) INFORMATION FOR SEQ ID NO: 15:

( i ) SEQUENCE CHARACTERISTICS:
( A ) LENGTH: 34 Nucleotides
( B ) TYPE: Nucleotide
( C ) STRANDEDNESS: Single
( D ) TOPOLOGY: Linear ( x i ) SEQUENCE DESCRIPTION: SEQ ID NO: 15:

GGTGTGTACA CACATTGGCG GTGGATGAGG TCGG    34

( 2 ) INFORMATION FOR SEQ ID NO: 16:

( i ) SEQUENCE CHARACTERISTICS:
( A ) LENGTH: 42 Nucleotides
( B ) TYPE: Nucleotide
( C ) STRANDEDNESS: Single
( D ) TOPOLOGY: Linear ( x i ) SEQUENCE DESCRIPTION: SEQ ID NO: 16:

GGGGCGCAGT TAGGTGTGAG GTGTGAGGTC ACGTGGGCTC    40

GG    42

( 2 ) INFORMATION FOR SEQ ID NO: 17:

( i ) SEQUENCE CHARACTERISTICS:
( A ) LENGTH: 40 Nucleotides
( B ) TYPE: Nucleotide
( C ) STRANDEDNESS: Single
( D ) TOPOLOGY: Linear ( x i ) SEQUENCE DESCRIPTION: SEQ ID NO: 17:

GGATGATATC CTCATGGCAG GGAATGGTGC GGGCTCCAGG    40

(2) INFORMATION FOR SEQ ID NO: 18:

(i) SEQUENCE CHARACTERISTICS:
        (A) LENGTH: 38 Nucleotides
        (B) TYPE: Nucleotide
        (C) STRANDEDNESS: Single
        (D) TOPOLOGY: Linear (xi) SEQUENCE DESCRIPTION: SEQ ID NO: 18:

```
GGATTTGATA TGGCAGGGAA TGGTGCGGGC TTCCCAGG                    38
```

(2) INFORMATION FOR SEQ ID NO: 19:

(i) SEQUENCE CHARACTERISTICS:
        (A) LENGTH: 96 Nucleotides
        (B) TYPE: Nucleotide
        (C) STRANDEDNESS: Single
        (D) TOPOLOGY: Linear (xi) SEQUENCE DESCRIPTION: SEQ ID NO: 19:

```
CGTACGGAAT TCGCTAGCNN NNNNNNNNN NNNNNNNNN                    40
NNNNNNNNN NNNNNNNNN NNNNNNNNN NNNNNNNCC                      80
ATCCCACCTC CACCTC                                            96
```

(2) INFORMATION FOR SEQ ID NO: 20:

(i) SEQUENCE CHARACTERISTICS:
        (A) LENGTH: 18 Nucleotides
        (B) TYPE: Nucleotide
        (C) STRANDEDNESS: Single
        (D) TOPOLOGY: Linear (xi) SEQUENCE DESCRIPTION: SEQ ID NO: 20:

```
CCTACCCAAT TCCCTAGC                                          18
```

(2) INFORMATION FOR SEQ ID NO: 21:

(i) SEQUENCE CHARACTERISTICS:
        (A) LENGTH: 18 Nucleotides
        (B) TYPE: Nucleotide
        (C) STRANDEDNESS: Single
        (D) TOPOLOGY: Linear (xi) SEQUENCE DESCRIPTION: SEQ ID NO: 21:

```
CACGTGGAGC TCGGATCC                                          18
```